US00PP22755P2

(12) United States Plant Patent
Egger

(10) Patent No.: US PP22,755 P2
(45) Date of Patent: May 22, 2012

(54) *SEDUM* PLANT NAMED 'RASPBERRY TRUFFLE'

(50) Latin Name: *Sedum telephium*
Varietal Denomination: Raspberry Truffle

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/931,951

(22) Filed: Feb. 14, 2011

(51) Int. Cl.
*A01H 5/00* (2006.01)

(52) U.S. Cl. ..... Plt./479

(58) Field of Classification Search ..... Plt./479
See application file for complete search history.

*Primary Examiner* — Annette Para
(74) *Attorney, Agent, or Firm* — Klarquist Sparkman, LLP

(57) ABSTRACT

A new and distinct cultivar of *Sedum* plant substantially as shown and described, with medium large, oblong, glossy purple brown leaves with cut edges, an upright, compact habit, showy maroon stems, rose pink flowers, and excellent vigor.

1 Drawing Sheet

Botanical denomination: *Sedum telephium.*
Variety designation: 'Raspberry Truffle'.
Parentage: *Sedum telephium* dark leaf OP.

The present invention relates to a new and distinct cultivar of *Sedum* and given the cultivar name of 'Raspberry Truffle'. *Sedum* is in the family Crassulaceae. *Sedum* 'Raspberry Truffle' originated from an open pollinated cross between a proprietary, unpatented dark leaf *Sedum telephium* as the seed parent and an unknown *Sedum telephium* as the pollen parent. Compared to the *Sedum telephium* seed parent, the new cultivar has a more upright habit, larger flower clusters, and longer, darker brown leaves. Compared to *Sedum* 'Chocolate Drop' (U.S. Plant patent application Ser. No. 12/798,839), the new cultivar has longer, darker leaves that are more distinctly toothed, purple brown rather than red brown, and has larger flower heads.

This new and unique *Sedum* is distinguished by:

1. medium large, oblong, glossy purple brown leaves with cut edges,
2. upright, compact habit,
3. showy maroon stems,
4. rose pink flowers,
5. and excellent vigor.

This new cultivar has been reproduced only by asexual propagation (division, cuttings, and tissue culture). Each of the progeny exhibits identical characteristics to the original plant. Asexual propagation by cuttings, division and tissue culture using standard techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a two-year-old *Sedum* 'Raspberry Truffle' growing in the ground in the garden in June in Canby, Oreg.

DETAILED PLANT DESCRIPTION

The following is a detailed description of the new *Sedum* cultivar based on observations of two-year-old specimens grown in the ground in full sun in the garden in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, 5$^{th}$ edition.

Plant:

*Type.*—Herbaceous perennial.
*Hardiness.*—USDA Zone 4 to 9.
*Size.*—Grows to 43 cm tall from the ground to the top of the foliage and 43 cm wide.
*Habit.*—Ascending, clumping.
*Vigor.*—Excellent.

Stem:

*Size.*—Grows to 28 cm long and 9 mm wide.
*Number.*—Plants have between 8 and 16 main stems from the crown.
*Internodes.*—3 mm to 4 mm long.
*Surface.*—Glabrous, shiny.
*Color.*—Greyed Purple 187A.

Leaf:

*Type.*—Simple.
*Arrangement.*—Opposite.
*Shape.*—Elliptic.
*Apex.*—Obtuse.
*Base.*—Auriculate.
*Venation.*—Pinnate.
*Margins.*—Irregularly dentate.
*Blade size.*—Grows to 7.7 cm long and 4 cm wide.
*Surface.*—Glabrous, glossy.
*Texture.*—Thick, succulent.
*Petiole.*—Leaves sessile.
*Leaf color.*—Topside between Greyed Purple 187A and N186B; bottom side Yellow Green 147C heavily tinted Greyed Purple 187A.

Inflorescence:

*Type.*—Terminal, corymbose, umbel-like.
*Size of inflorescence.*—Grows to 12 cm wide and 15 cm deep.
*Number of flowers.*—About 500 per stem.
*Peduncle.*—Grows to 8 cm tall and 5 mm wide, Greyed Purple 187B, glabrous.

*Branching.*—3 main branches per stem.

*Bloom period.*—July in Canby, Oreg.

Flower bud:

*Size.*—4 mm wide, 6 mm long.

*Description.*—Ovoid.

*Color.*—Greyed Purple 186C with the tip 187A.

Flower:

*Type.*—Complete, actinomorphic.

*Shape.*—Rotate.

*Size.*—7 mm deep and 9 mm wide.

*Color.*—Greyed Purple 186C with center Red Purple 59B.

*Corolla description.*—9 mm wide and 7 mm deep, 5 petals, each lanceolate, 7 mm long and 2.5 mm wide, entire, glabrous on both sides, tip keeled, Greyed Purple 186D on both sides, inside main vein Greyed Purple 186A and tip Greyed Purple 187A.

*Calyx description.*—Stellate, 4 mm deep and 4 mm wide, 5 small ovate lobes, divided ¾ to the base, 3 mm long and 1 mm wide at the base, entire, acute, glabrous and Greyed Green 197A on both sides.

*Stamen description.*—10 in number, 6.5 mm long, filaments 6 mm long, Red Purple 61A, anthers undehisced Greyed Purple N186A, pollen Yellow Orange 18C.

*Pistil description.*—5 separate prominent carpels, each 6 mm deep and 1 mm wide, Red Purple 59C.

*Fragrance.*—None.

*Lastingness.*—Each inflorescence lasts for about 3 weeks.

Fruit:

*Type.*—Ventrally dehiscent follicle, erect, attenuate.

*Fertility.*—Unknown, none seen.

Seed: None seen.

Disease and pest resistance or tolerance: All *Sedum* species are susceptible to root rots with poor drainage. They are also susceptible to mealybug, scale, slugs and snails. None of these insect problems have been noted on the new variety. There are no known resistances.

I claim:

1. A new and distinct cultivar of *Sedum* plant as herein illustrated and described.

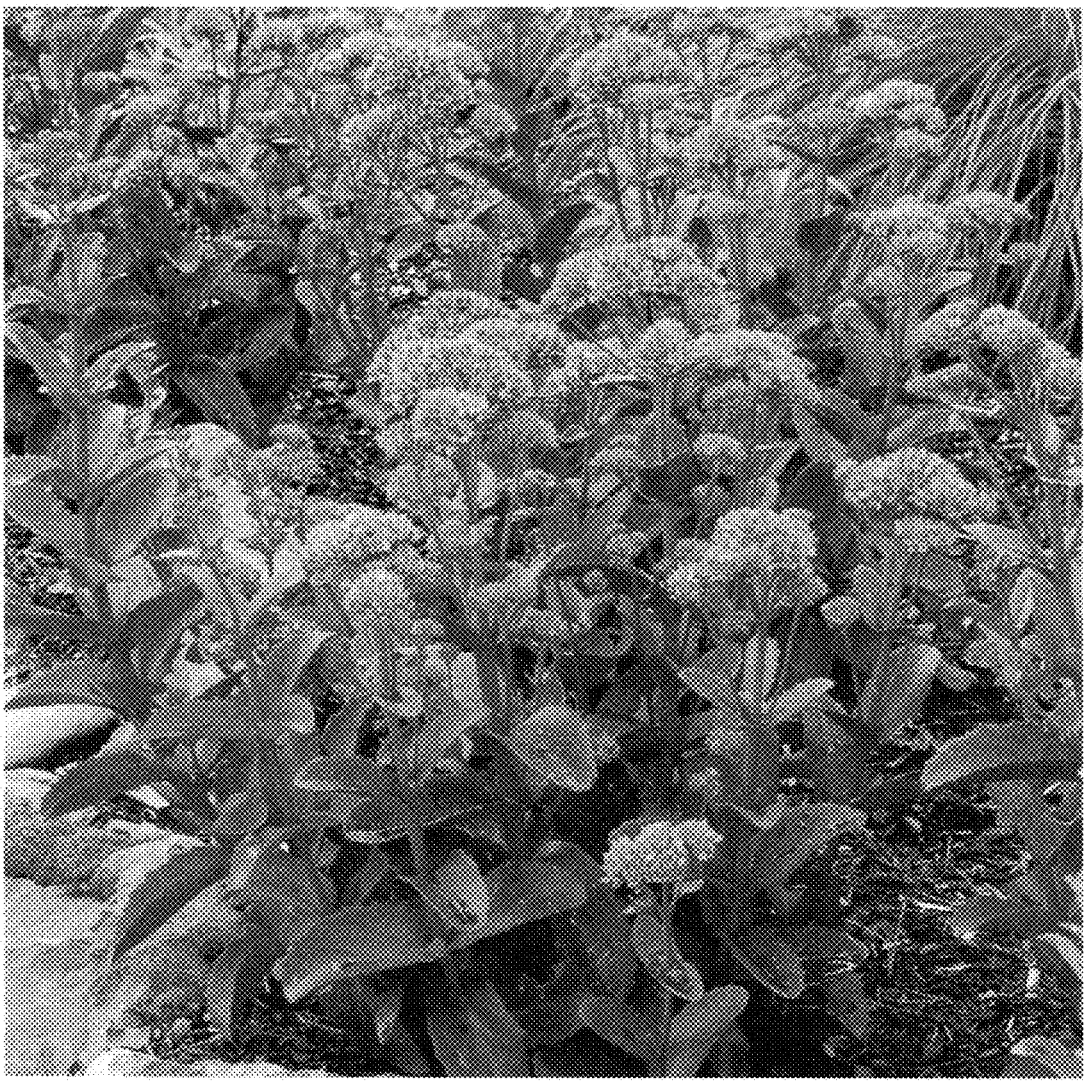

* * * * *